United States Patent [19]

Tuke

[11] Patent Number: 4,851,006
[45] Date of Patent: Jul. 25, 1989

[54] ACETABULUM

[75] Inventor: Michael A. Tuke, Burpham, England

[73] Assignee: Finsbury (Instruments) Limited, Chessington, England

[21] Appl. No.: 184,340

[22] Filed: Apr. 21, 1988

[30] Foreign Application Priority Data

Apr. 22, 1987 [GB] United Kingdom ................. 8709535

[51] Int. Cl.4 ............................ A61F 2/34; F16B 2/22
[52] U.S. Cl. ....................................... 623/22; 411/411
[58] Field of Search ...................... 623/16, 18, 19, 20, 623/22, 23; 411/411, 453, 414, 415

[56] References Cited

U.S. PATENT DOCUMENTS

| 3,840,904 | 10/1974 | Tronzo | 623/23 |
| 4,044,403 | 8/1977 | D'Errico | 623/22 |
| 4,479,271 | 10/1984 | Bolesky et al. | 623/20 |
| 4,536,894 | 8/1985 | Galante et al. | 623/16 |
| 4,666,450 | 3/1987 | Kenna | 623/22 |
| 4,715,859 | 12/1987 | Schelhous et al. | 623/22 |
| 4,722,870 | 2/1988 | White | 623/16 |

FOREIGN PATENT DOCUMENTS 0149425 7/1985 European Pat. Off. .
0237751 9/1987 European Pat. Off. .
2911754 10/1980 Fed. Rep. of Germany .

OTHER PUBLICATIONS

Joint Medical Product Corporation, "The S.ROM Acetabular System", Journal of Bone & Joint Surg., 68-A, Apr. 1986, p. 91.

Primary Examiner—Richard J. Apley
Assistant Examiner—David J. Isabella
Attorney, Agent, or Firm—Lee & Smith

[57] ABSTRACT

An artificial acetabulum is described comprising a metal cup having on its outer surface means for locking the cup in a pelvic cavity, a hollow locating peg projecting from the base of the cup and integral therewith, and a liner within the cup and having a projection which fits within the hollow peg.

10 Claims, 2 Drawing Sheets

ACETABULUM

This invention relates to an artificial acetabulum of the type used in hip replacement operations.

The efficient functioning of the hip joints is extremely important to the well being and mobility of the human body. Each hip joint is constituted by the upper portion of the upper leg bone (femur) which terminates in an offset bony neck surmounted by a ball-headed portion which rotates within a socket (acetabulum) in the hip bone. Diseases such as rheumatoid- and osteo-arthritis can cause erosion of the cartilage lining the acetabulum so that the ball of the femur and hip bone rub together causing pain and further erosion. Bone erosion causes the bones themselves to attempt to compensate and reshape, thus giving a misshapen joint which may well cease to function altogether.

The replacement of the hip joint by an artificial implant is widely practised. In such an operation, not only is a prosthesis placed in a suitably formed femoral cavity, but also an artificial acetabulum is required to be inserted in the pelvis. It is desirable to fit an artificial acetabulum to the pelvis with as little destruction of bone as possible. Ideally the attachment is accomplished without the use of cement so as to eliminate such problems as cracking and loosening of the cement and, consequently, the joint, causing wear, and also the danger of cement finding its way into the joint itself. Several cementless acetabulums have been proposed. Some comprise an outer cup of suitable metal, such as titanium, and an inner bearing liner surface of suitable plastics such as polyethylene. The outer cup has been given a heavily screw threaded outer contour in an attempt to maximise the keying to the pelvis. In such designs the cup is typically shaped as a truncated cone and the large threads engage in cancellous bone. The inner liner has been snap fitted into the metal cup and often sits into an aperture extending through the base of the metal cup thus allowing the polyethylene to contact bone.

Such devices are subject to a number of problems. Firstly, the provision of a substantial screw thread on almost the entire outer face of the cup is difficult and expensive to manufacture. As a result it has not been possible to make such threaded cups with an outer contour approaching the spherical contour desirable if one is to remove only the minimum of the pelvic bone. Thus the outer contour has been substantially more barrel or conical shaped than desirable, with a flattened end. The pelvic bone is comparatively thin and reaming a cavity to take such an undesirably large cup is invasive and potentially dangerous. This is especially so in that it is very difficult to get the angle of insertion of the acetabulum (i.e. the "attitude") exactly right for any given patient. Secondly the use of such a shape leads to a bearing of load by the outer sides of the cup in the region of the thread and not adjacent the flattened top. This "stress shielding" effect has the result that the unloaded bone tends to weaken or disappear as it is not being correctly loaded. Thirdly, the snapped-in plastics liner actually contacts the bone at the base of the cup and, being a flowable material under pressure, tends to flow through the aperture in the cup thus destroying the lining. This problem becomes more acute if the bone itself is disappearing or weakened in that region due to the stress shielding effect described above.

There is clearly a need for an improved acetabulum and the present invention seeks to overcome some or all of these problems.

According to this invention there is provided an artificial acetabulum comprising a metal cup having on its outer surface means for locking the cup in a pelvic cavity, a hollow locating peg projecting from the base of the cup and integral therewith and a liner within the cup and having a projection which fits within the hollow peg.

Preferably the outer surface of the metal cup is part-spherical. Preferably the locking means comprises a minimal amount of screw thread (for example approximately one turn of thread) which thread is preferably formed only in that region adjacent the edge of the cup and that region adjacent the peg is free of thread. With such a thread formation in combination with a part-spherical cup, it is possible to implant the cup so that this is seated on the sub-chondral plate and so that the thread engages in cortical bone without destroying the sub-chondral plate.

The metal cup is preferably of titanium or of a titanium alloy, although other metals compatible with the human body may be used such as stainless steel. The metal surface of the cup may be provided with a coating of a bone-compatible material, for example a bone-compatible ceramic such as hydroxyapatite. It may also have at least one screw hole for reception of a bone fixation screw.

The liner is preferably made of a physiologically compatible plastics material, such as polyethylene, although other materials, generally also plastics, with a low coefficient of friction can be used. Ultra high molecular weight polyethylene is a preferred material from which to make the liner.

One form of the invention will now be described with reference to the accompanying drawings wherein.

Figure 1:
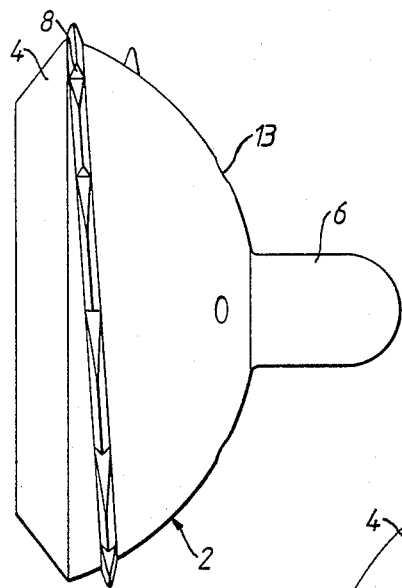
FIG. 1 is a side view of the outer cup of an artificial acetabulum according to the invention without its liner.
Figure 2:
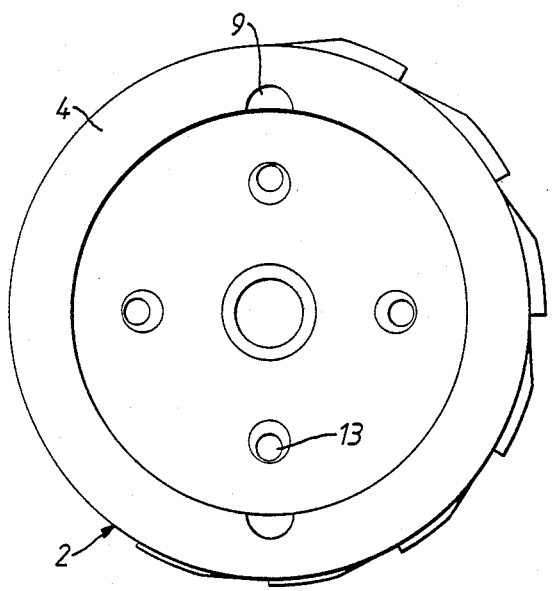
FIG. 2 is a front view of the cup of FIG. 1.
Figure 3:
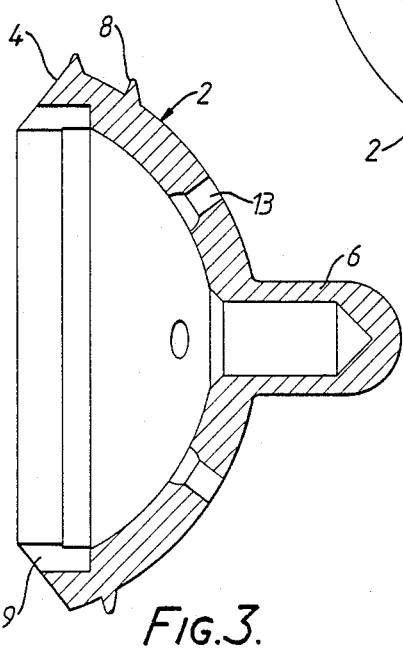
FIG. 3 is a section through the cup of FIG. 1.
Figure 4:
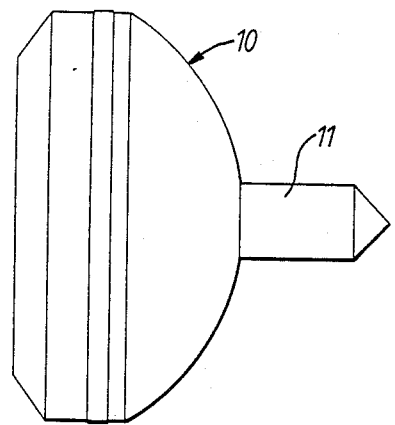
FIG. 4 is a side view of the liner for the cup of FIGS. 1 to 3.
Figure 5:
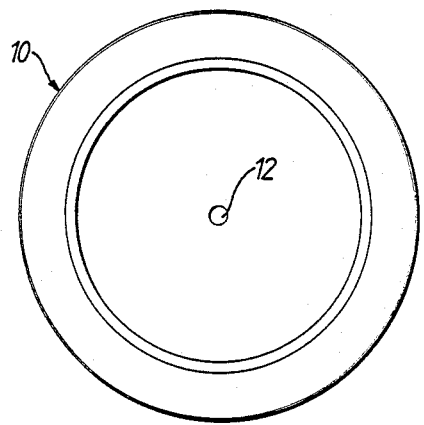
FIG. 5 is a front view of the cup of FIG. 4.
Figure 6:
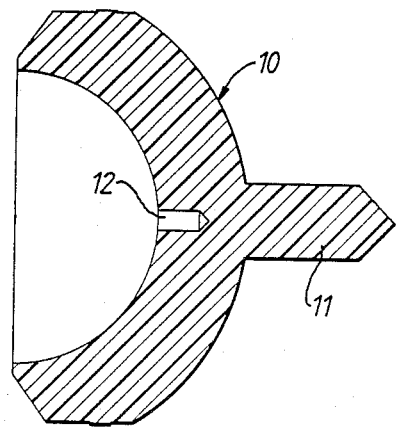
FIG. 6 is a section through the cup of FIG. 4.

The artificial acetabulum shown in the drawings comprises an outer cup 2, preferably of titanium or of a titanium alloy, which is substantially part-spherical with a chamfered edge 4 and has, at the base of the cup, an integral hollow peg 6. A toothed self tapping screw thread 8 is provided adjacent the chamfered edge 4, only a portion of the outer surface of the cup 2 being threaded. The amount of thread is sufficient to lock the cup in a pelvic cavity with just one rotation. Typically there is approximately one complete turn of screw thread. Cut outs 9 are provided in the chamfered edge 4 for insertion. As shown in FIGS. 4 to 6, a liner 10, shaped to lodge snugly in cup 2, is provided, conveniently of ultra high molecular weight polyethylene. Liner 10 has a projection 11 which enables it to be fitted easily into hollow peg 6 of cup 2 so that the two parts snap securely together. A bore 12 is provided in the base of liner 10 for location of an extraction screw.

In use a suitable tool is used to make a locating bore to receive the superomedial peg 6 and position the acetabulum at the correct attitude for the patient undergoing surgery. There is no need for the acetabulum to be tapped first. The cup of the actual acetabulum is then screwed home in the correct position with minimum bite into the bone of the pelvis. Inclusion of recessed screw holes 13 in the cup 2 enables sighting of the cup being driven fully home. Hence the surgeon is enabled to have visualisation of the whole seating during this step. The screw holes 13 further allow optional extra fixation with bone screws prior to fitting the plastics liner 10. The spherical outer surface of the cup means that only minimum bone removal has been necessary and the absence of large portions of screw thread ensures that load is not unduly transferred to the screw thread but is borne by the whole outer surface of the cup including the area immediately adjacent the peg 6. Furthermore there is no danger of the plastics liner contacting the bone as it is entirely surrounded by the cup 2. Additionally the improved low profile design of the illustrated artificial acetabulum avoids the danger of impingement of the femoral neck.

What is claimed:

1. An artificial acetabulum comprising (1) a metal cup having an edge, an outer bone engaging surface extending from the edge to a base remote from the edge, self-tapping screw thread means functionally equivalent to approximately one turn of thread, formed on the outer surface adjacent the edge for engagment in cortical whereby the cup is locked in its final position in a pelvic cavity with just one rotation of said metal cup without destroying the sub-chondral plate, and a hollow peg projecting from the base of the cup and integral therewith, said hollow peg being coaxial with the axis of the self-tapping screw thread means and being adapted to fit in a prepared locating bore in a pelvic bone so as to form a pivot about which the cup can be rotated during implantation, and (2) a liner within the cup and having a projection which fits within the hollow peg.

2. An artificial acetabulum according to claim 1, in which the outer surface of the metal cup is part-spherical.

3. An artificial acetabulum according to claim 1, in which the self-tapping screw thread means approximately one turn of thread.

4. An artificial acetabulum according to claim 1, in which the self-tapping screw thread means is formed only on a region of the outer surface of the cup adjacent the edge of the cup and a region of the outer surface of the cup adjacent the peg is free of thread.

5. An artificial acetabulum according to claim 3, in which the self-tapping screw thread means is formed only on a region of the outer surface of the cup adjacent the edge of the cup and a region of the outer surface of the cup adjacent the peg is free of thread.

6. An artificial acetabulum according to claim 1, in which the metal cup is made from titanium or from titanium alloy.

7. An artificial acetabulum according to claim 1, in which the metal cup is provided on said outer surface with a coating of a bone-compatible ceramic.

8. An artificial acetabulum according to claim 7, in which the bone-compatible ceramic is hydroxyapatite.

9. An artificial acetabulum according to claim 1, in which the liner is made of ultra high molecular weight polyethylene.

10. An artificial acetabulum according to claim 1; in which the metal cup is provided with at least one screw hole for reception of a bone fixation screw.

* * * * *